United States Patent [19]
Huang et al.

[11] Patent Number: 5,440,929
[45] Date of Patent: Aug. 15, 1995

[54] ULTRASONIC DEVICE FOR MEASURING THICKNESS OF A TANK BOTTOM FLAT PLATE

[75] Inventors: Hai-Yang Huang, Chutung Hsinchu; Mu-Chung Peng; Yung-How Wu, both of Hsinchu, all of Taiwan

[73] Assignee: Industrial Technology Research Institute, Taiwan

[21] Appl. No.: 156,038

[22] Filed: Nov. 22, 1993

[51] Int. Cl.⁶ ............................................ G01N 29/26
[52] U.S. Cl. ..................................................... 73/628
[58] Field of Search ................. 73/597, 620, 627, 628, 73/635, 632

[56] References Cited

U.S. PATENT DOCUMENTS

| | | |
|---|---|---|
| 3,612,920 | 10/1971 | Bantz . |
| 3,844,166 | 10/1974 | Carossi et al. . |
| 3,914,987 | 10/1975 | Bickel et al. . |
| 4,123,943 | 11/1978 | Roddy et al. . |
| 4,324,141 | 4/1982 | Stearn . |
| 4,353,257 | 10/1982 | Vrba et al. . |
| 4,429,576 | 2/1984 | Norris ................................. 73/627 |
| 4,509,369 | 4/1985 | Kuljis ................................. 73/628 |
| 4,541,064 | 9/1985 | Livingston . |
| 4,658,648 | 4/1987 | Roddeck et al. . |
| 4,719,808 | 1/1988 | Baumann et al. . |
| 5,009,103 | 4/1991 | Sato et al. . |
| 5,067,352 | 11/1991 | Floret ................................. 73/628 |

FOREIGN PATENT DOCUMENTS

| | | |
|---|---|---|
| 3410954 | 9/1984 | Germany . |
| 3340693 | 5/1985 | Germany . |
| 3441894 | 7/1986 | Germany . |
| 3634374 | 4/1988 | Germany . |
| 4002884 | 4/1991 | Germany . |
| 7514910 | 4/1991 | Netherlands . |
| 561087 | 10/1977 | U.S.S.R. . |
| 608050 | 4/1978 | U.S.S.R. . |
| 1105757 | 7/1984 | U.S.S.R. . |
| 629806 | 9/1987 | U.S.S.R. . |
| 1446469 | 12/1988 | U.S.S.R. . |
| 1467392 | 3/1989 | U.S.S.R. . |
| 1640547 | 4/1991 | U.S.S.R. . |

*Primary Examiner*—Hezron E. Williams
*Assistant Examiner*—Christine K. Oda
*Attorney, Agent, or Firm*—Marshall & Melhorn

[57] ABSTRACT

An ultrasonic system is provided for measuring the thickness of steel plates used in the bottom of oil storage tanks and other similar applications. When the bottom plate corrodes, the potential for leakage occurs. The ultrasonic system can be used to monitor the corrosion of bottom plates in areas which are generally inaccessible, such as the bottom of oil storage tanks. The ultrasonic system includes a probe drive frame having multiple brackets for supporting a plurality of ultrasonic probes. A pulse generator and multi-channel scanner are connected to the probes. A processing unit reads and processes the signals from the probes to calculate the thickness of the plate and to warn of potential leakage problems caused by corrosion of the plate. The system can be operated from a remote location outside the oil storage tanks, which minimizes the time and expense in monitoring the plate.

5 Claims, 13 Drawing Sheets

ULTRASONIC DEVICE FOR MEASURING THICKNESS OF A TANK BOTTOM FLAT PLATE

BACKGROUND OF THE INVENTION

1. Field of the Invention

The present invention relates to an ultrasonic measuring device, especially to an ultrasonic measuring device for measuring the thickness of a large flat plate.

2. Description of Prior Art

Oil tanks are critically important equipment for the petrochemical industry. Usually they are used to store petroleum or petroleum products. They can range in volume from several gallons to millions of barrels.

Large oil tanks are mostly situated on soil or specially treated ground. Due to dirt, water, and other impurities that rest at the bottom of tanks, the upper side of the steel plates at the bottom of the tanks rusts continuously. On the outside, ground water and rainwater wear down the lower side of the plates so that pitting and rusting develop. When the steel plates rust through, oil or petroleum will leak and pollute the environment. Therefore, measuring the residual depth (thickness) of the bottom plates of oil tanks is very important.

The upper side of the bottom plates can be visually inspected after oil contents of the tank are discharged. However, the lower side of the bottom plates cannot be so inspected. Usually this is done by ultrasonic equipment. However, the procedure involves some difficulties, including:

1) When the upper and lower sides of the bottom plates are seriously corroded, conventional ultrasonic probes cannot couple with the plates well, or
2) When the area of the bottom plates is too large to be inspected point by point within a short period of time.

As a result, inspections cannot be practiced routinely. Therefore, leakage by accident happens sometimes. The pursuit of a better method to inspect flat panel tank bottom is important today.

SUMMARY OF THE INVENTION

The primary object of the present invention is to provide an inspection system for detecting the depth of the bottom plate of oil tanks using ultrasonic detection to monitor the corrosion of the bottom plate, thus preventing oil leakage.

The secondary object of the present invention is to provide a depth detection system for detecting the depth of a plate using ultrasonic detection that only requires inputting into the data processing unit, the speed of sound in the material of the plate.

Another object of the present invention is to provide a depth detection system that can detect the depth at a plurality of points simultaneously and accurately, and display the results at once for a user to evaluate the extent of corrosion.

The objects mentioned will be fulfilled by providing an ultrasonic measuring device to measure the depth of a large flat plate, the device comprising a gear, having supporting means and wheels, one of the wheels being coupled with an encoder, the encoder being capable of sending encoded signals corresponding to the rotation of the wheel; a pulser-receiver, to continuously generate an ultrasonic signal and a synchronizing signal simultaneously, and for receiving a response signal of the ultrasonic signal, then amplifying said response signal for output; a plurality of ultrasonic probes, for emitting ultrasonic waves according to the ultrasonic signal, then receiving echos of the ultrasonic waves and producing the response signal of the echos, mounted on the supporting means so that the probes can be directed to any direction; a multi-scanner, for forcing the pulser-receiver to couple with one of the probes in sequence according to a controlling signal; a gated peak detector, for receiving the response signal and the synchronizing signal from said pulser-receiver, and gating the response signal in order to extract the response signals of first two echos; a signal processing unit, for receiving the synchronizing signal from the pulser-receiver, the gated response signals of the first two echos from the gated peak detector, and the encoder signal from the encoder, and calculating the depth of the flat plate according to sound speed and the interval between the response signals of the first two echos, and calculating distance of movement of said gear according the encoder signal, the signal processing unit being capable of sending the controlling signal to the multi-scanner.

BRIEF DESCRIPTION OF THE DRAWINGS

The present invention can be more fully understood by referring to the following detailed description and accompanying drawings, which form an integral part of this application.

DETAILED DESCRIPTION OF THE PREFERRED EMBODIMENT

Figure 1:
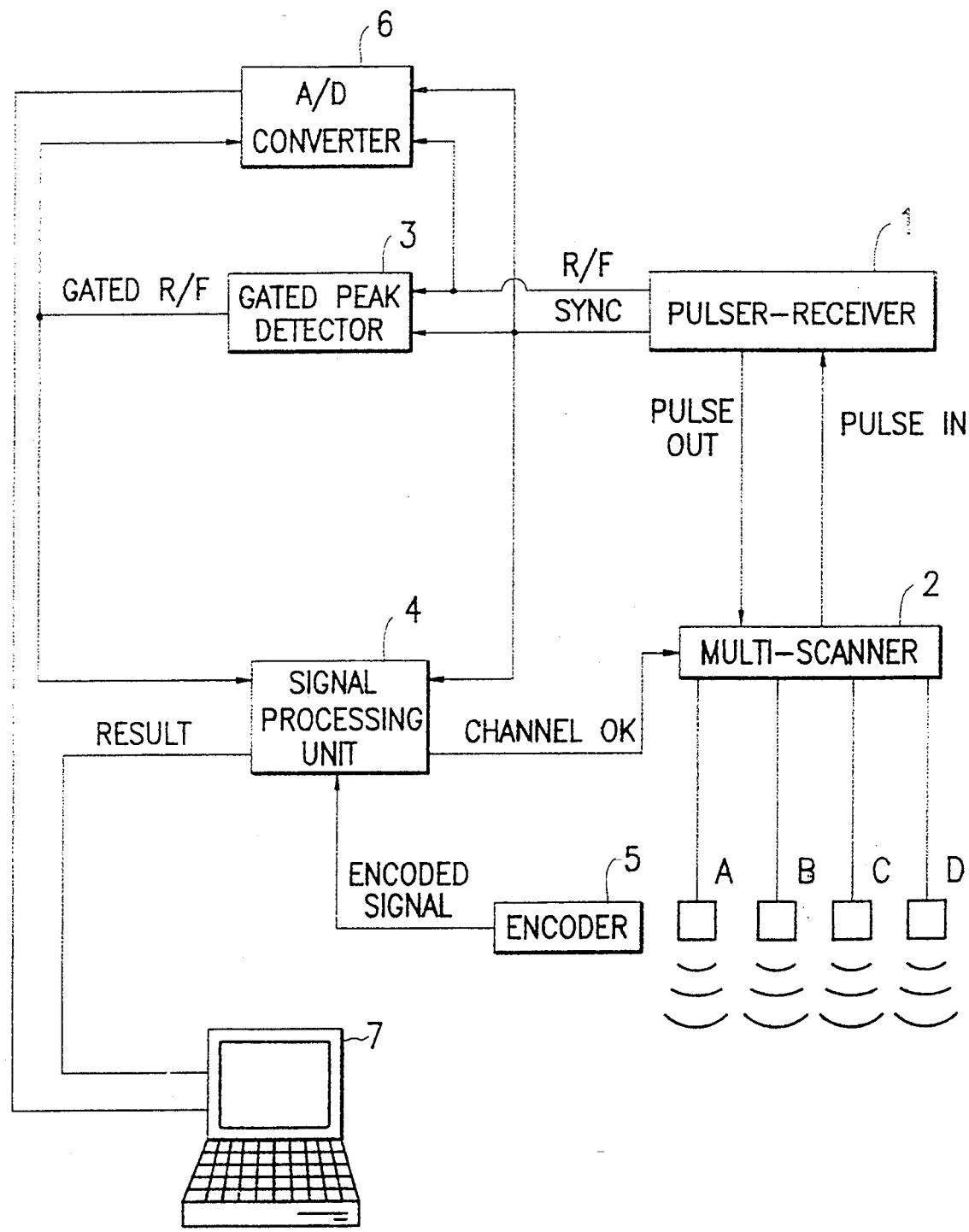
FIG. 1 is a block diagram schematically showing the system according to the present invention.
Figure 2:
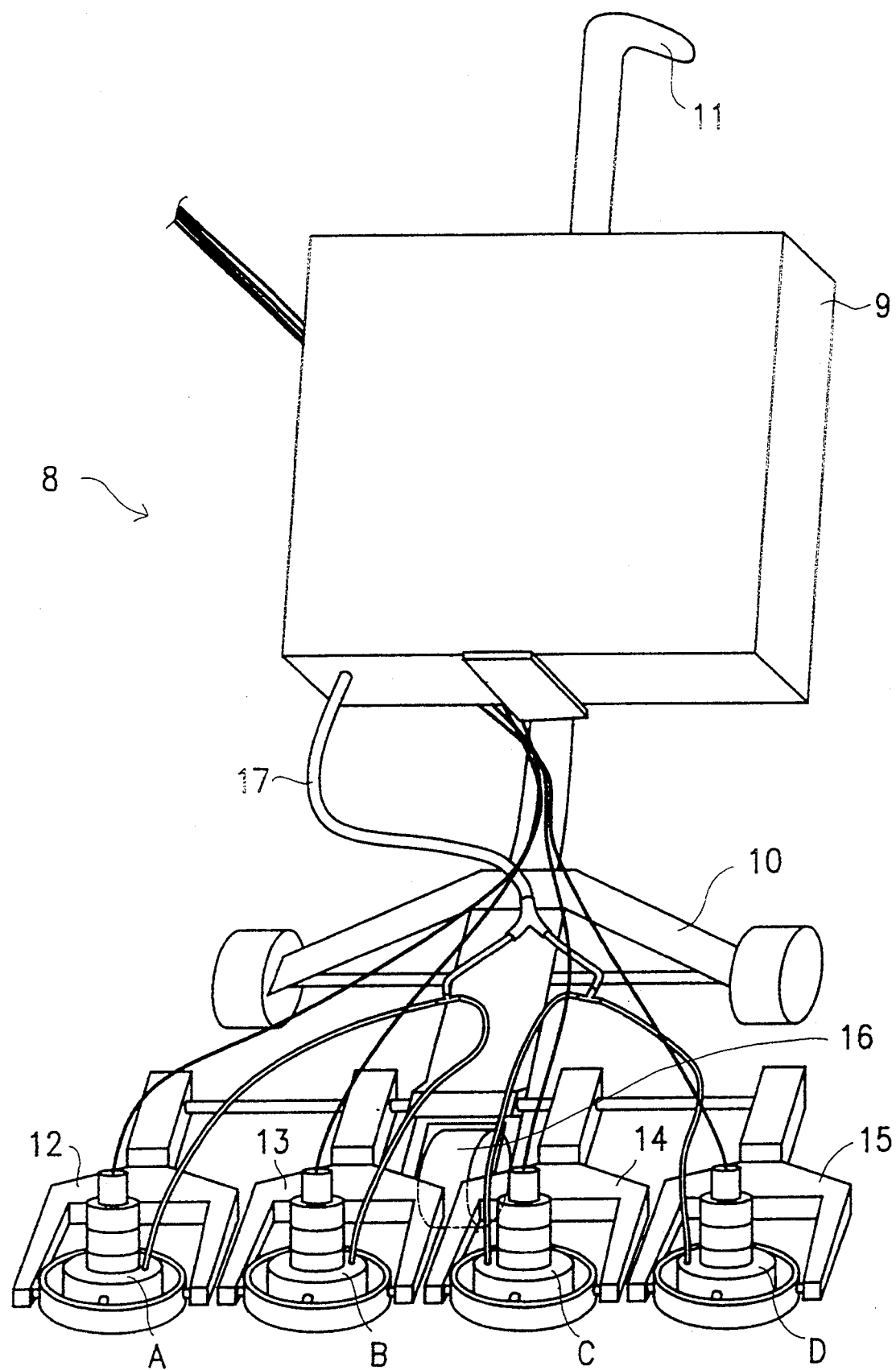
FIG. 2 is a perspective diagram showing the gear of the system.

Please refer to FIG. 1 and FIG. 2. The present invention essentially consists of a pulser-receiver 1, a multi-scanner 2, a plurality of ultrasonic probes A, B, C and D, a gated peak detector 3, a signal processing unit 4, a probe drive frame 8, a sound conducting fluid supply device 9, a data processing unit 7, and an analog-to-digital converter 6.

Pulser-receiver 1 has one input terminal: pulse in, and three output terminals, including pulse out, sync, and R/F. Pulser-receiver 1 is capable of continuously producing ultrasonic pulse signals, and outputting the pulse signals through the pulse out terminal. The echos of the pulse signals are received from the pulse in terminal, and then amplified and outputted through the R/F terminal by the pulser-receiver 1. Each time one of the pulse signals is emitted, a synchronizing signal is simultaneously emitted through the sync terminal by the pulser-receiver 1 to keep other devices synchronized with the pulse signals. The structure of the pulser-receiver 1 is well known in the art, so a detailed configuration of the pulser-receiver 1 is not shown.

Ultrasonic probes A, B, C and D are capable of receiving the ultrasonic pulse signals from the pulser-receiver 1, and transforming them into pulsive ultrasonic waves. The pulsive ultrasonic waves pass through sound conducting fluid and reach the front surface of the plate to be detected. A front surface echo occurs and is received by the probes. The unreflected component of the pulsive ultrasonic waves passes through the plate and reaches the back surface of the plate. A back surface echo occurs and is received by the probes. The pulsive ultrasonic waves are reflected between the front surface and the back surface until they fade away. Therefore, the probes receive a front surface echo and a plurality of back surface echos. The echos are transformed into echo signals and sent to pulser-receiver 1 by the probes.

In the present invention, for measuring different positions with one detecting system, ultrasonic probes A, B, C and D are not coupled to the pulser-receiver 1 directly. Multi-scanner 2 is used to couple the probes. Multi-scanner 2 is like a selective switch, for coupling the ultrasonic probes A, B, C and D to the pulser-receiver 1 in turn. When the multi-scanner 2 receives a signal from the terminal of channel clock, it will switch to the next probe. With the aid of multi-scanner 2, four ultrasonic probes A, B, C and D can be coupled to one pulser-receiver, therefore greatly lowering the cost of the system. In addition, more probes can be attached to the multi-scanner 2 in order to detect more positions at a time, thus magnifying the effectiveness of the entire system.

Gated peak detector 3 has two input terminals, R/F, sync., and one output terminal, gated R/F. The echo signals of the pulsive ultrasonic waves are amplified by the pulser-receiver 1, then received by gated peak detector 3 through the R/F terminal. The gated peak detector 3 is capable of extracting the front surface echo and the first back surface echo, which comes after the front surface echo, from the echo signals by adjusting gate delay and gate width. The extracted signals will be sent out through the gated R/F terminal. It should be noted that the gated peak detector is also a conventional device that can be purchased on the market, therefore the details of the gated peak detector will not be further discussed.

Figure 3:
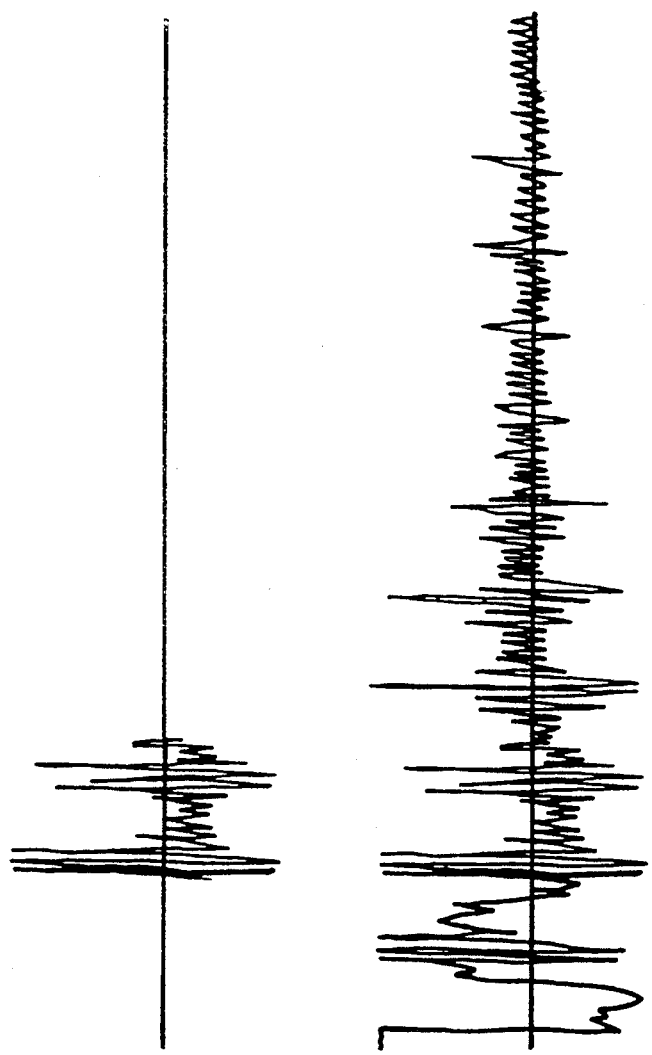
FIG. 3 is a diagram showing the signal of a front surface echo and a back surface echo.

For monitoring the gated R/F signals, an analog-to-digital converter 6 is used in the preferred embodiment. Analog-to-digital converter 6 receives the sync signal and the R/F signal from the pulser-receiver 1, and the gated R/F signal from the multi-scanner 2. These signals are digitized by the analog-to-digital Converter 6 and sent to data processing unit 7 for display. As depicted in FIG. 3, R/F signal is shown at the lower side, the gated R/F signal is shown at the upper side. A user can observe the display and adjust the delay time and the gate width of the gated peak detector 3 for better extraction. Analog-to-digital converter 6 is a conventional device that will not be further discussed.

Probe drive frame 8, as shown in FIG. 2, has a chassis 10 and a handle 11. Chassis 10 has three wheels. One of the wheels, wheel 16, is coupled to an encoder 5. When wheel 16 rotates as the probe drive frame 8 is sliding, encoder 5 will generate encoder signals according to the rotation angle of the wheel 16. Four supporting brackets 12, 13, 14, and 15 are set at the front of the probe drive frame 8, which support the ultrasonic probes A, B, C and D respectively. The supporting brackets are capable of supporting the probes while providing degrees of freedom, so that the probes can follow the direction of the surface of the plate to be detected.

Sound conducting fluid supply device 9 is arranged on the top of the probe drive frame 8, and filled with sound conducting fluid (in the present embodiment, the sound conducting fluid is water). Tube 17 is set to guide the sound conducting fluid to the probes.

Figure 4:
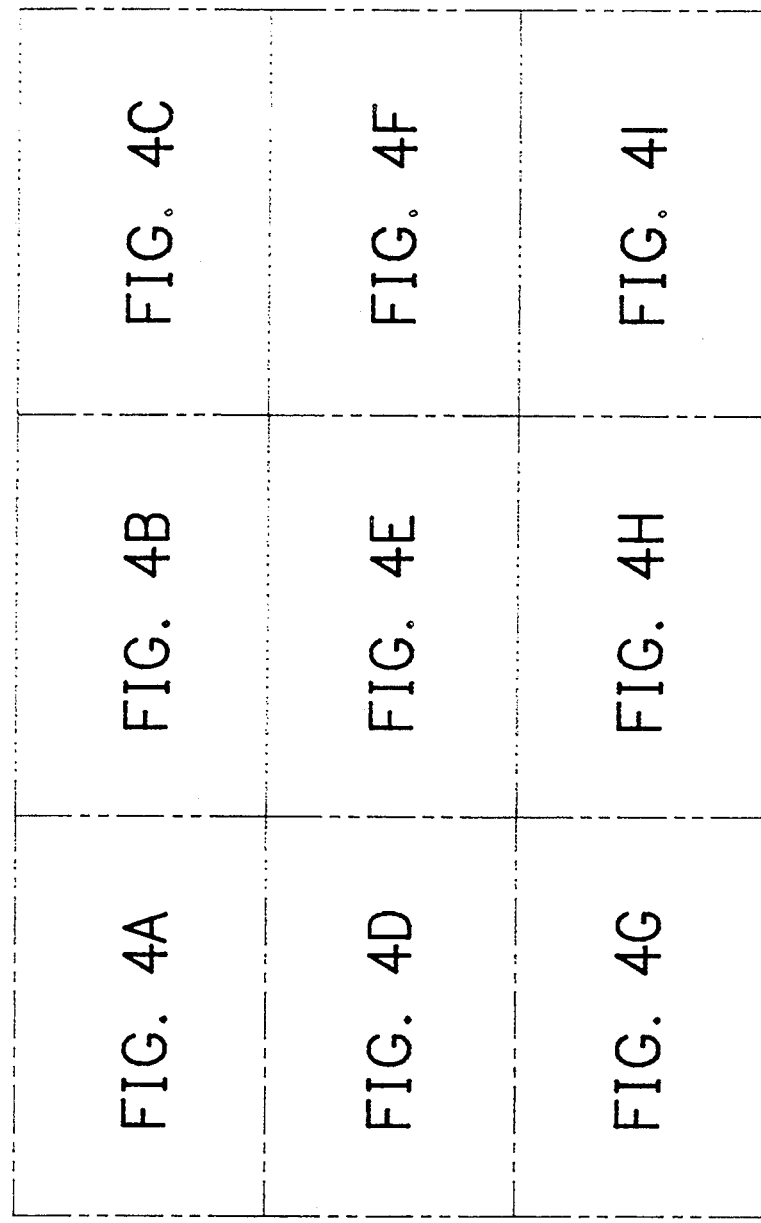
FIG. 4 is an assembly diagram showing the relationship of FIG. 4A through 4I, which show the configuration of the signal processing unit.
Figure 4A:
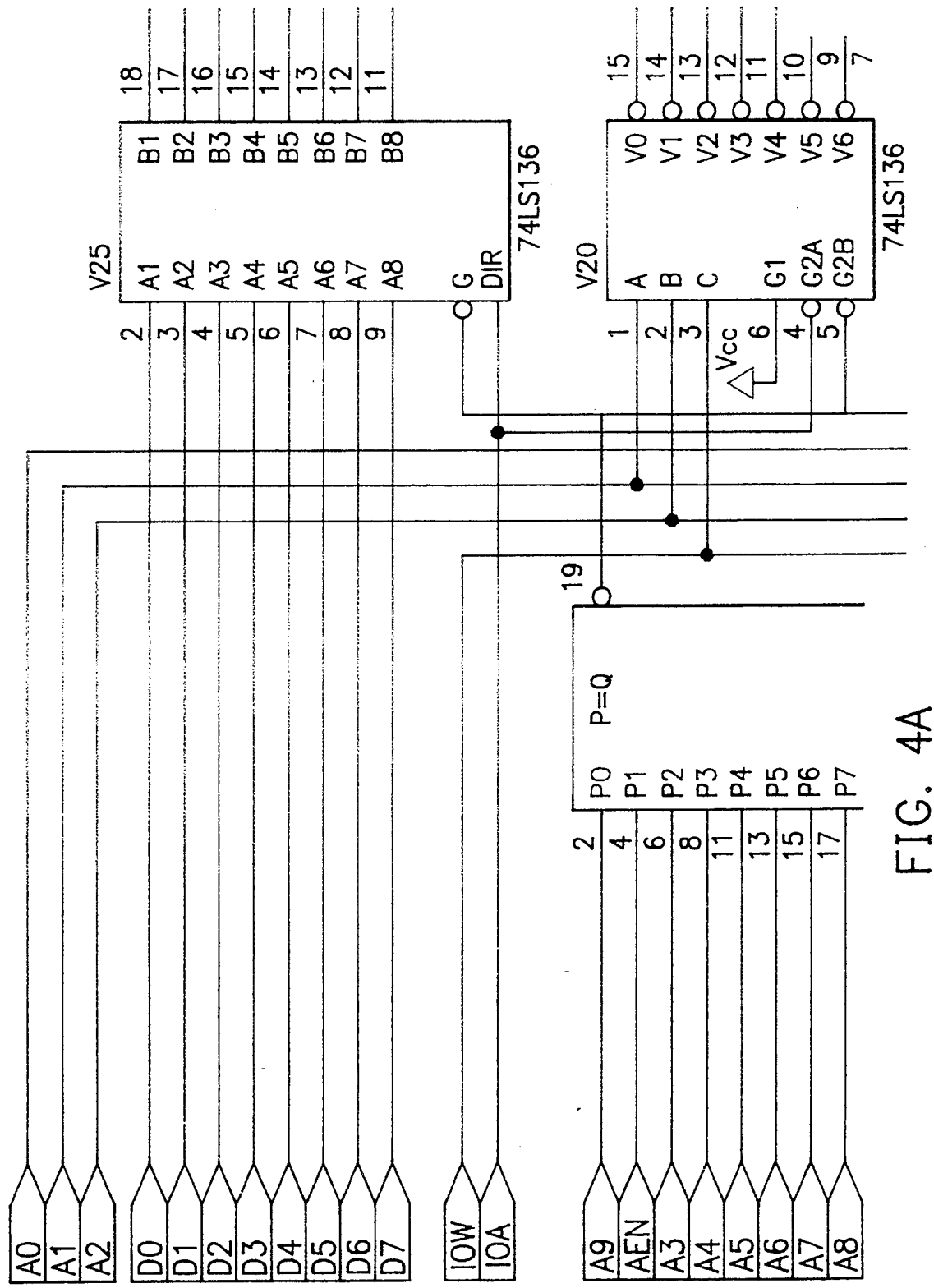
FIG. 4A is a schematic view showing a portion of the signal processing unit as indicated in FIG. 4.
Figure 4B:
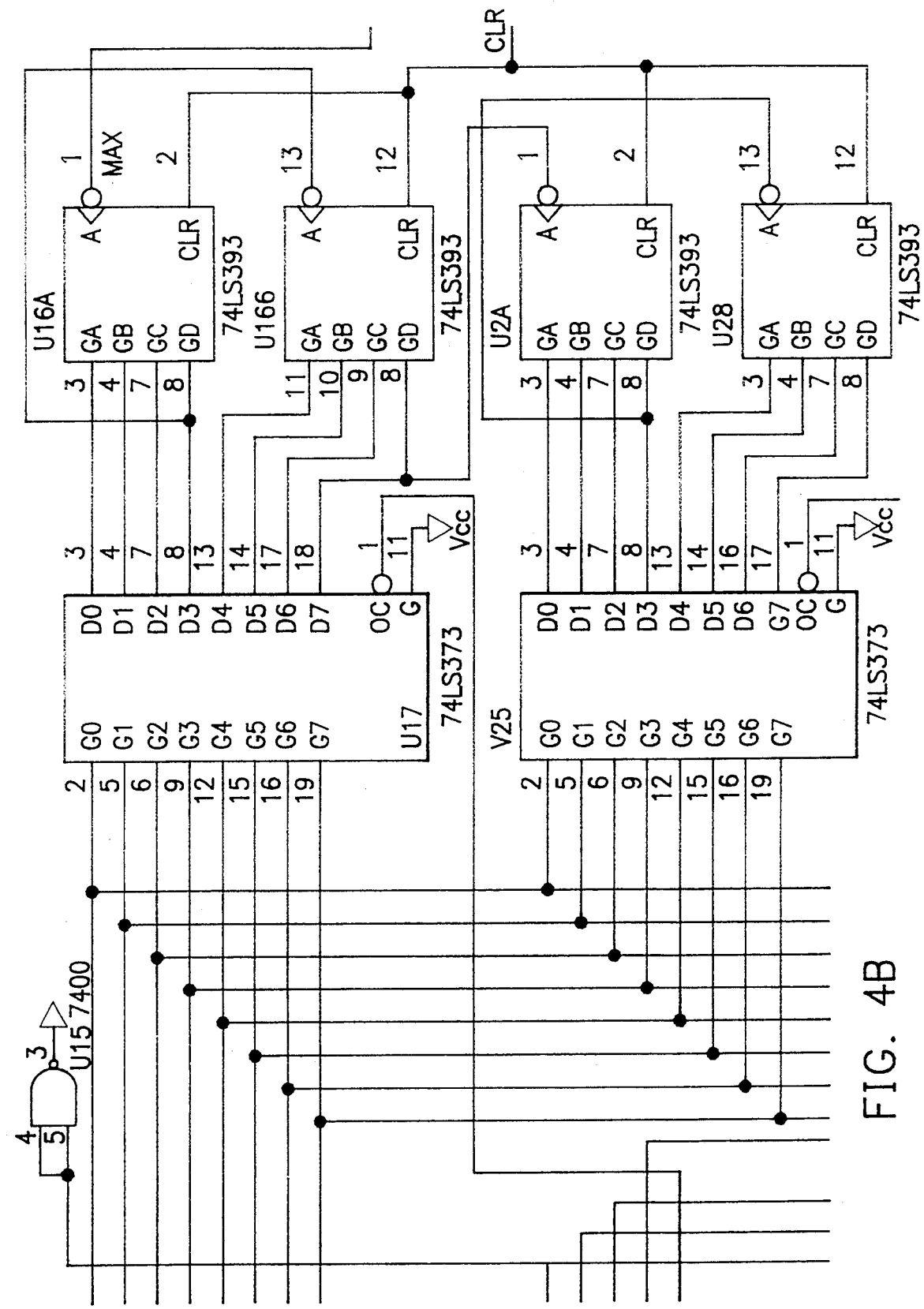
FIG. 4B is a schematic diagram showing a further portion of the signal processing unit as indicated in FIG. 4.
Figure 4C:
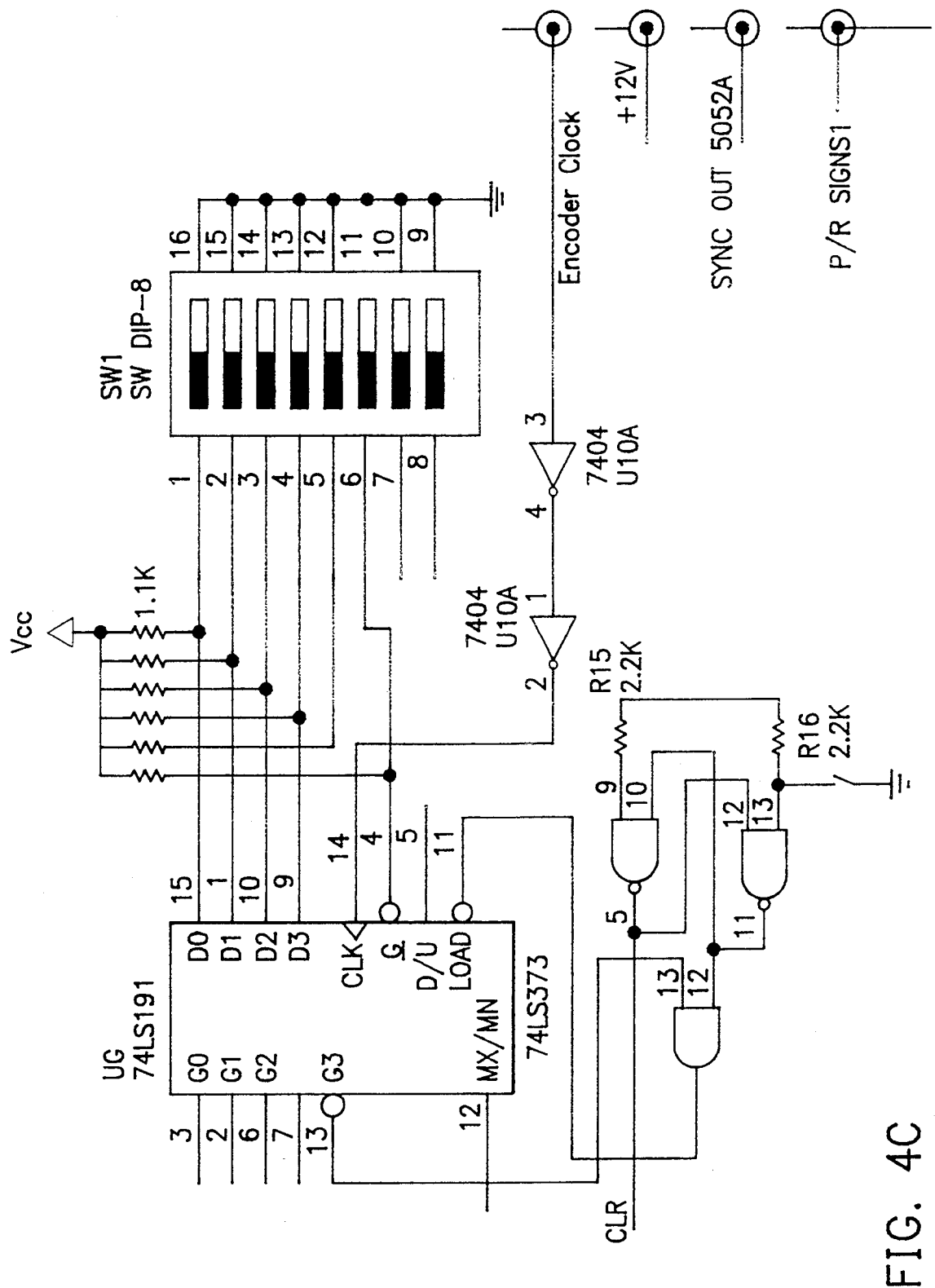
FIG. 4C is a schematic drawing showing a further portion of the signal processing unit shown in FIG. 4.
Figure 4D:
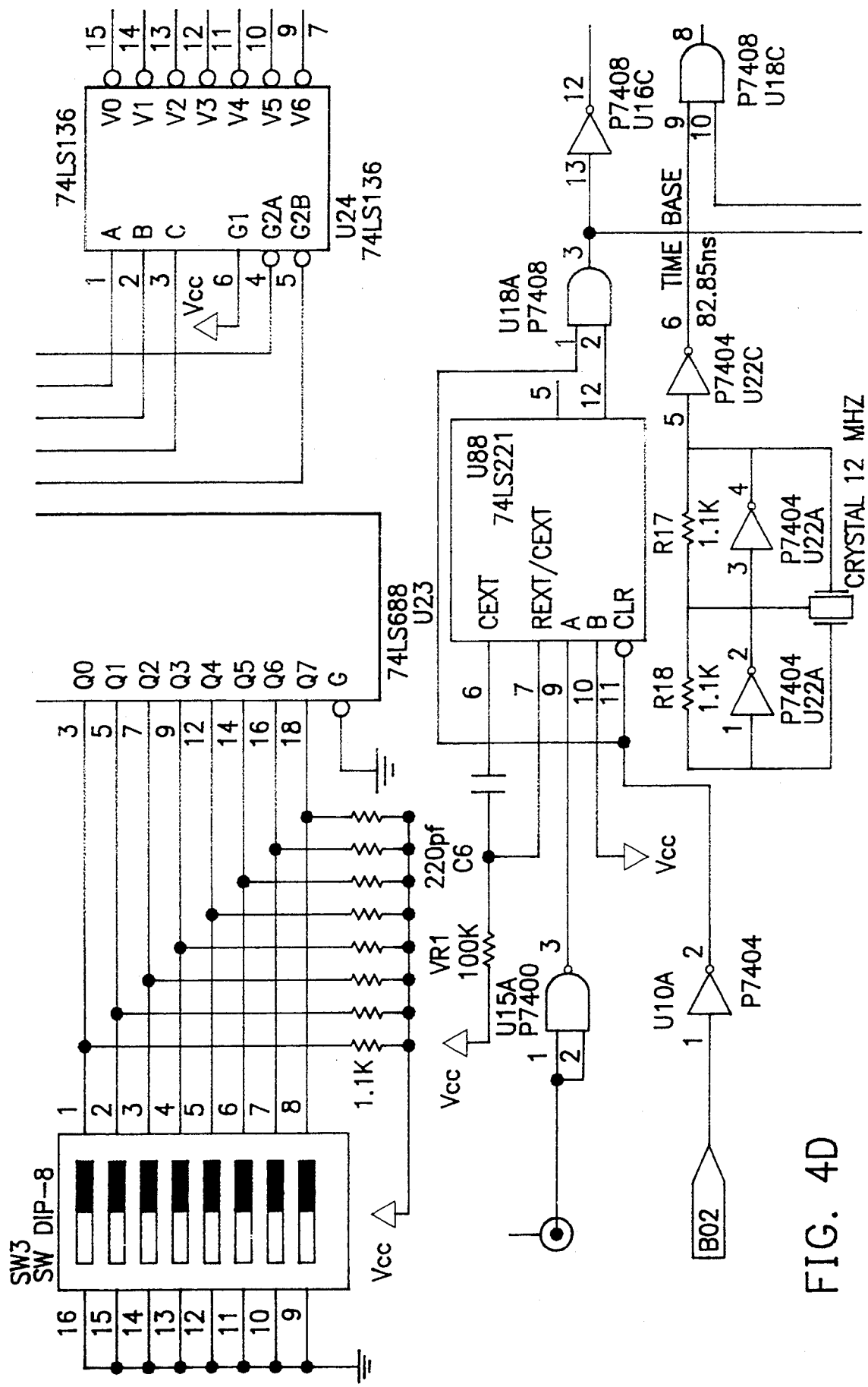
FIG. 4D is a schematic drawing showing a further portion of the signal processing unit shown in FIG. 4.
Figure 4E:
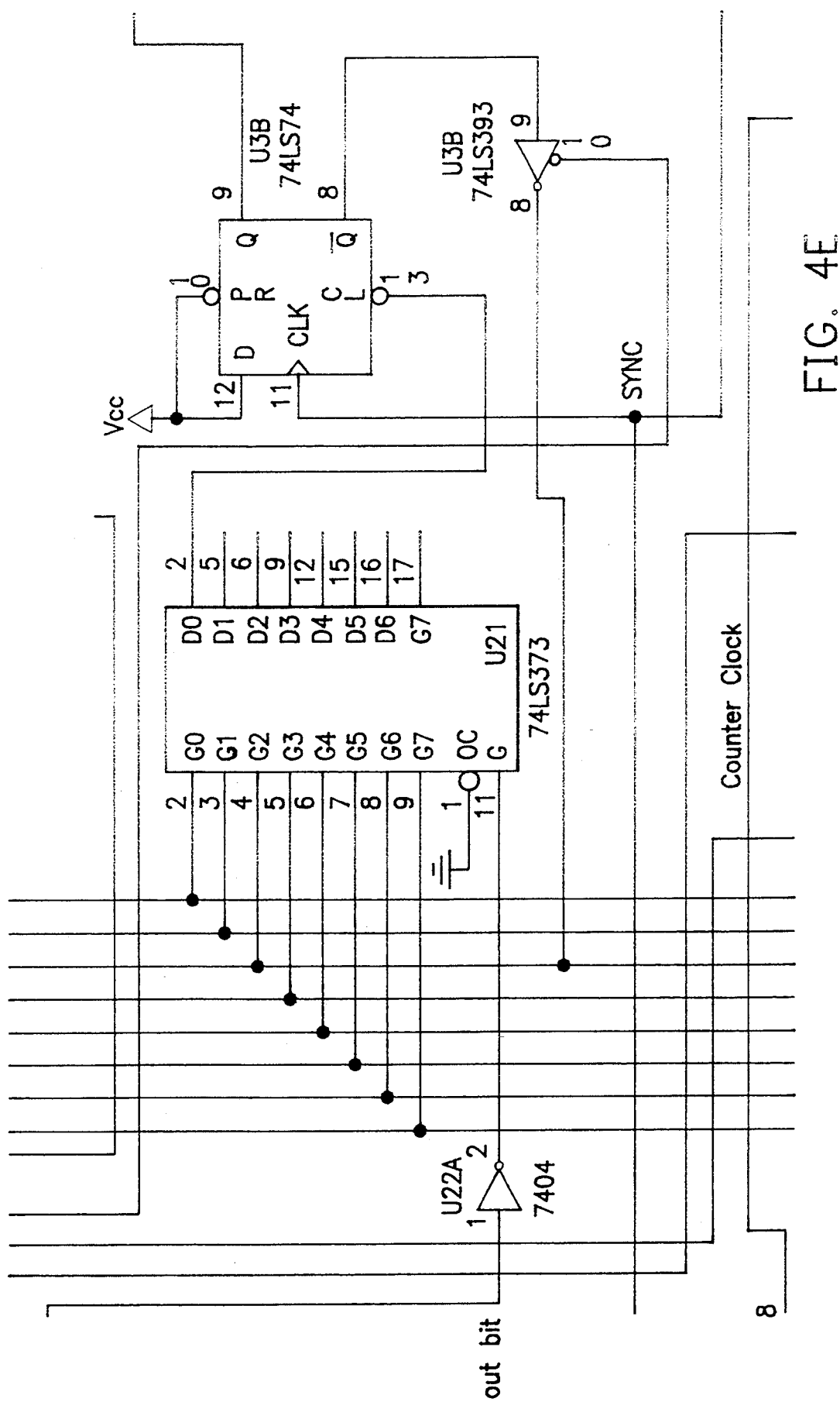
FIG. 4E is a schematic drawing showing a further portion of the signal processing unit shown in FIG. 4.
Figure 4F:
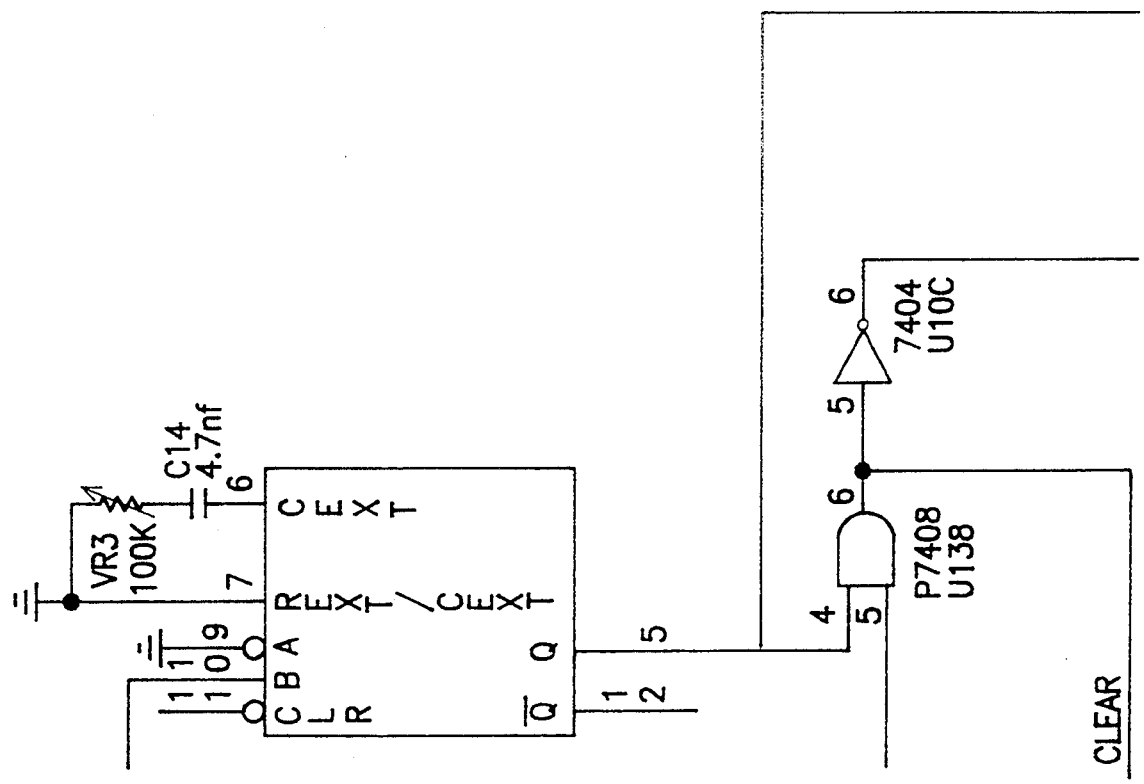
FIG. 4F is a schematic drawing showing a further portion of the signal processing unit shown in FIG. 4.
Figure 4G:
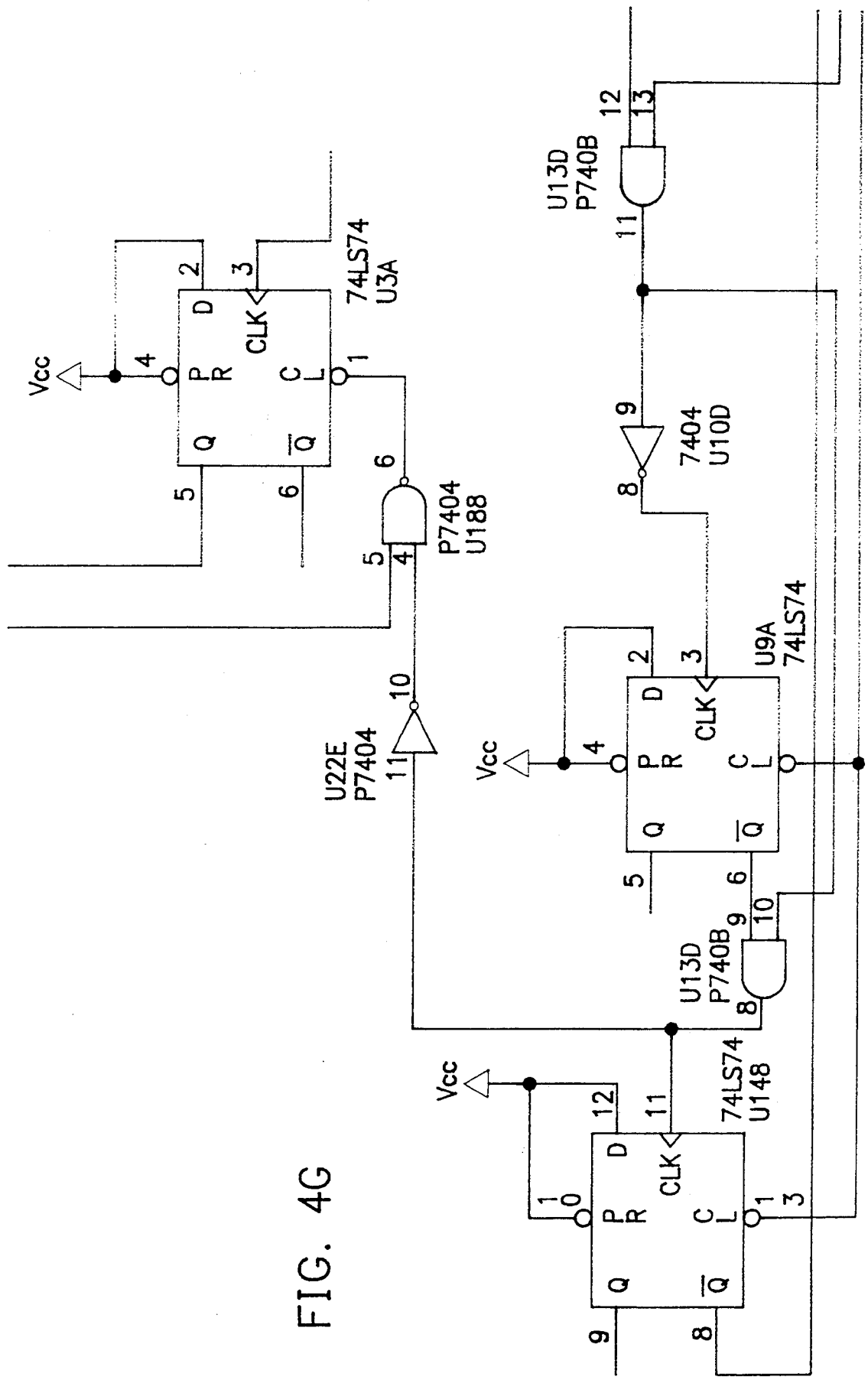
FIG. 4G is a schematic drawing showing a further portion of the signal processing unit shown in FIG. 4.
Figure 4H:
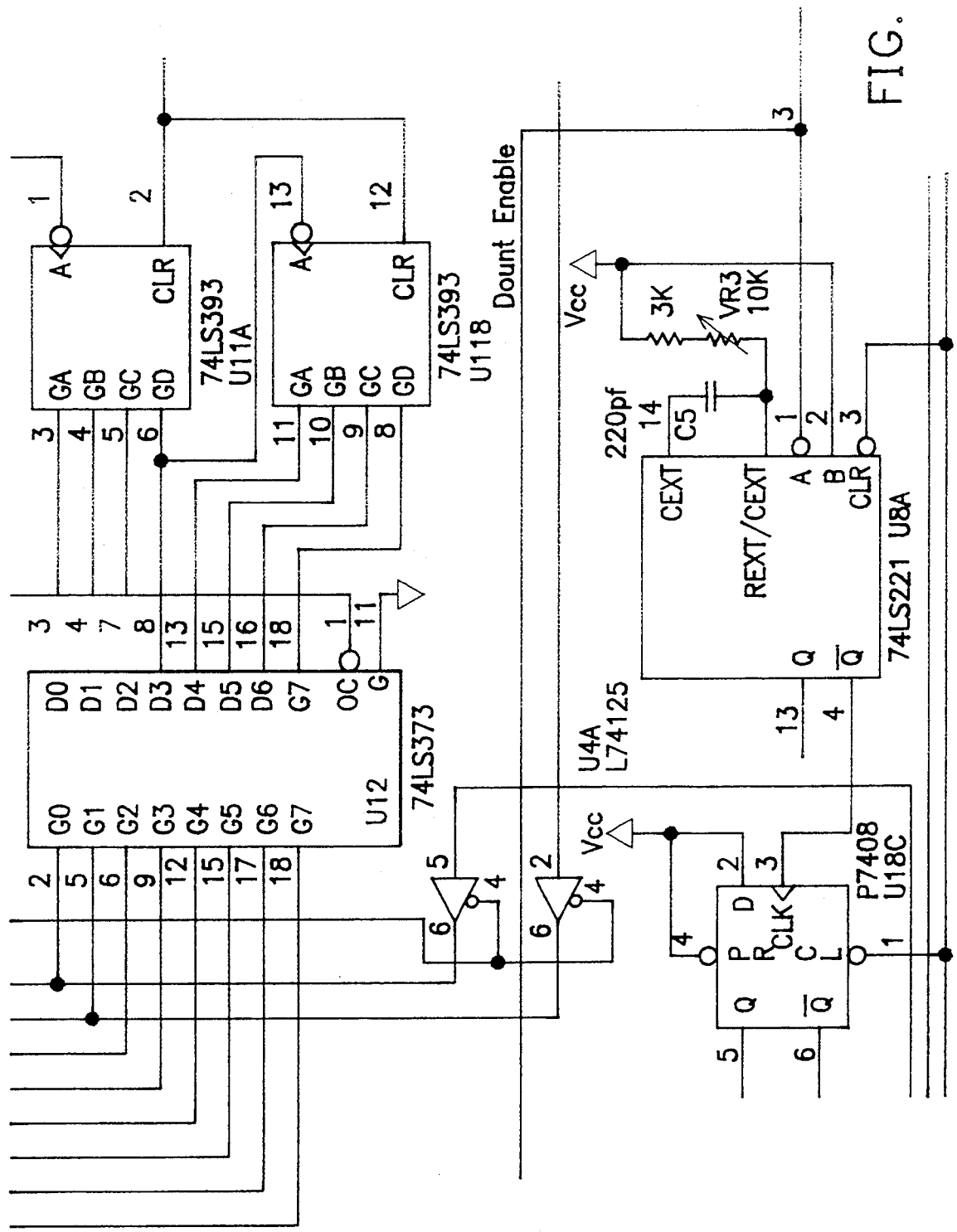
FIG. 4H is a schematic drawing showing a further portion of the signal processing unit shown in FIG. 4.
Figure 4I:
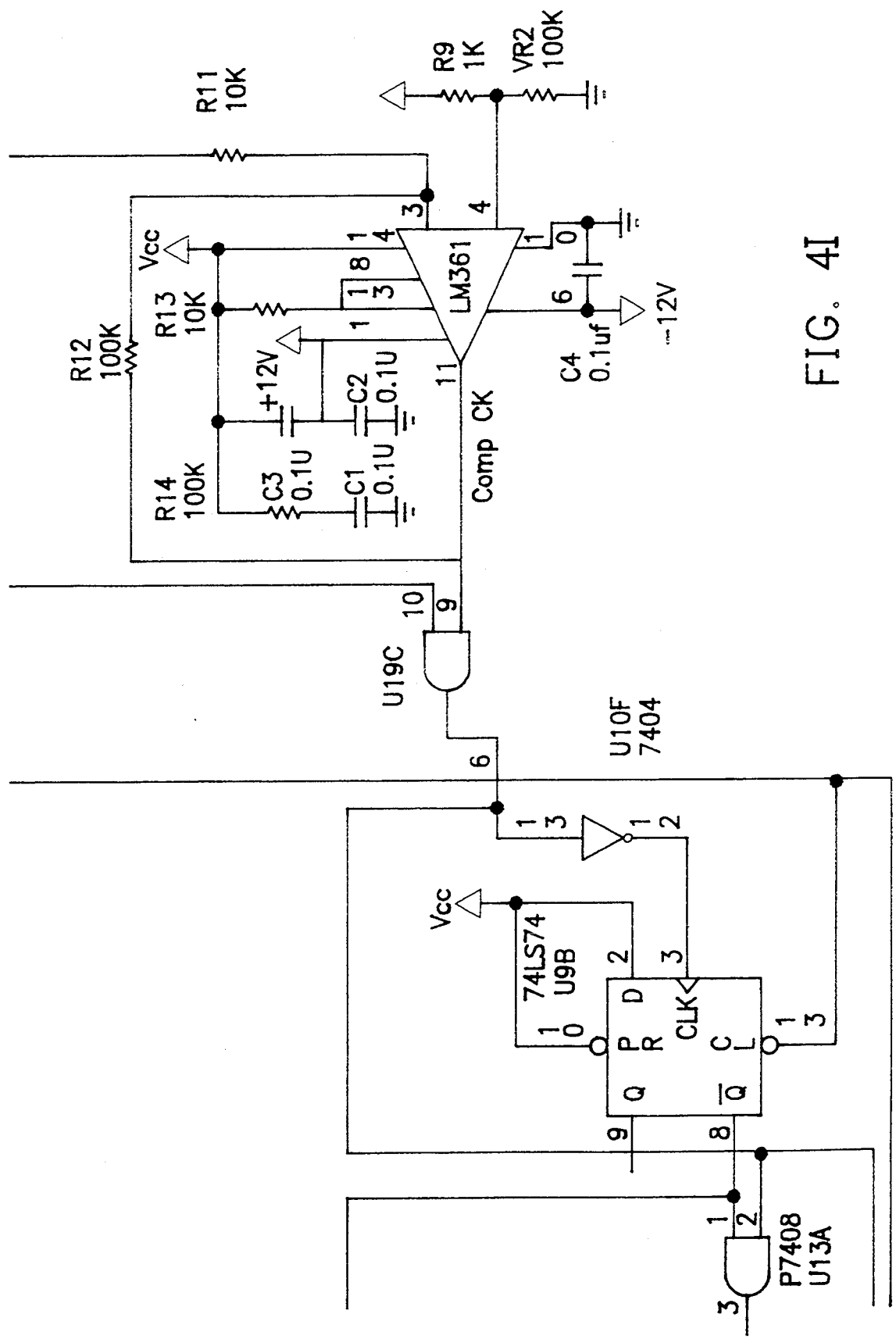
FIG. 4I is a schematic drawing showing a further portion of the signal processing unit shown in FIG. 4.

Signal processing unit 4 has three input terminals: sync 18, gated R/F 19, encoder signal 20, and two output terminals: 21 and result 22. The detailed configuration of circuit of the signal processing unit 4 is shown in FIG. 4. The signal processing unit 4 receives the front and back surface echos from the gated R/F terminal. The analog signals are converted to digital signals by the converter circuits 23 shown in FIG. 4. The digital output from the converter circuits 23 and an oscillation signal from oscillator 24 are processed in the logic circuits 25 in FIG. 4 to obtain the mean time between the front and block surface echos. The mean time is then divided by two and multiplied by the speed of sound in the material of the plate, therefore the depth of the plate where the probe located is determined. Signal processing unit 4 sends control signals from the channel ck output terminal 21 to the multi-scanner 2 in order to switch the ultrasonic probes A, B, C and D in sequence, therefore obtaining the depth data at the probe location. According to the encoder signal received at input terminal 20, signal processing unit 4 can determine the distance of movement of the probe drive frame 8. The signal processing unit 4 repeats the detecting procedures each time after the probe drive frame 8 has travelled a predetermined distance. Thus, the depth data of the plane along the trace of the probe drive frame 8 is obtained. All the depth data is sent out through the result terminal 22 to the data processing unit 7. In the present embodiment, data processing unit 7 is a personal computer. The data processing unit 7 collects and stores all data, for further processing or for statistical use. The depth data can be displayed to show the condition of corrosion of the plate after detection is completed. The plate can then be reinforced where corrosion occurs in order to prevent leakage.

While the invention has been described in terms of what is considered to be the most practical and preferred embodiment, it is to be understood that the invention need not be limited to the disclosed embodiment. On the contrary, said invention is intended to cover various modifications and similar arrangements included within the spirit and scope of the appended claims, the scope of which should be accorded the broadest interpretation so as to encompass all such modifications and similar structures.

What is claimed is:

1. An ultrasonic measuring device for measuring the thickness of a large flat plate having an upper surface and a lower surface, said ultrasonic measuring device comprising:
  a) a probe drive frame having a chassis and at least two wheels mounted on the chassis for supporting said frame on the upper surface of the flat plate;
  b) means for driving said probe drive frame over the upper surface of the flat plate;
  c) an encoder mounted on one of the wheels, said encoder transmitting an encoder signal corresponding to the movement of the wheel on which said encoder is mounted over the upper surface of the flat plate;
  d) a plurality of ultrasonic probes mounted on the chassis of said probe drive frame, each of said plurality of probes including a transmitter means for generating and emitting a directed beam of ultrasonic waves toward the flat plate upon receipt of an ultrasonic signal, and including a receiver means for receiving a single echo from the upper surface of the flat plate and a plurality of echoes from the lower surface of the flat plate and transforming said single echo from the upper surface and said plurality of echoes from the lower surface into response signals;
  e) a pulser-receiver in electrical communication with said plurality of ultrasonic probes, said pulser receiver transmitting ultrasonic signals to said ultrasonic probes, generating a synchronizing signal, receiving the response signals from the ultrasonic probes, and amplifying the response signals to generate amplified response signals for output transmittal;
  f) a gated peak detector in electrical communication with said pulser-receiver for receiving the amplified response signals and the synchronizing signal from the pulser-receiver, said gated peak detector gating the amplified response signals to extract the upper surface echo and a first lower surface echo to generate gated response signals;
  g) a processing unit in electrical communication with said encoder, said pulser-receiver, and said gated peak detector, said processing unit receiving the encoder signal from said encoder, the synchronizing signal from said pulse-receiver and the gated response signals from said gated peak detector, and said processing unit calculating a thickness of the flat plate according to the gated response signals and a known speed of sound value for the flat plate, and calculating a position of said plurality of ultrasonic probes according to the encoder signal, whereby the thickness of the flat plate is determined along the path of the probes over the upper surface of the flat plate.

2. The ultrasonic measuring device as claimed in claim 1, further comprising a multi-scanner connected between said plurality of ultrasonic probes and said pulser-receiver, said processing unit transmitting and said multi-scanner receiving a control signal from said processing unit, said multi-scanner selectively transmitting the ultrasonic signals from said pulser-receiver to each of said ultrasonic probes and transmitting the response signals from each of said ultrasonic probes to the pulser-receiver in sequence according to the control signal from said processing unit, whereby said processing unit calculates the thickness of the flat plate and the position on the upper surface of the flat plate for said each of said plurality of ultrasonic probes.

3. The ultrasonic measuring device as claimed in claim 1, wherein said probe drive frame includes a sound conducting fluid device, mounted on said probe drive frame, for supplying a sound conducting fluid to said probes.

4. The ultrasonic measuring device as claimed in claim 1, further comprising a data processing means, in electrical communication with said process unit, for receiving, storing, processing and displaying the thickness calculations and the position calculations of the processing unit according to a preprogrammed routine.

5. The ultrasonic measuring device as claimed in claim 4, further comprising an analog-to-digital converter for receiving the synchronizing signal and the amplified response signals from said pulser-receiver, and the gated response signals from said gated peak detector, said analog-to-digital converter digitalizing and transmitting to said data processing means for monitoring, the synchronizing signal, the amplified response signals and the gated response signals.

* * * * *